(12) United States Patent
Kameshima et al.

(10) Patent No.: US 10,992,883 B2
(45) Date of Patent: Apr. 27, 2021

(54) RADIATION IMAGING SYSTEM

(71) Applicant: CANON KABUSHIKI KAISHA, Tokyo (JP)

(72) Inventors: Toshio Kameshima, Kawasaki (JP); Hideyuki Okada, Honjo (JP); Eriko Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 360 days.

(21) Appl. No.: 15/767,299

(22) PCT Filed: Nov. 8, 2016

(86) PCT No.: PCT/JP2016/083104
§ 371 (c)(1),
(2) Date: Apr. 10, 2018

(87) PCT Pub. No.: WO2017/082250
PCT Pub. Date: May 18, 2017

(65) Prior Publication Data
US 2018/0295294 A1    Oct. 11, 2018

(30) Foreign Application Priority Data
Nov. 13, 2015 (JP) .............................. JP2015-223337

(51) Int. Cl.
*H04N 5/32* (2006.01)
*G01T 7/00* (2006.01)
(Continued)

(52) U.S. Cl.
CPC ............. *H04N 5/32* (2013.01); *A61B 6/4233* (2013.01); *A61B 6/542* (2013.01); *A61B 6/545* (2013.01); *G01T 7/00* (2013.01); *H05G 1/44* (2013.01)

(58) Field of Classification Search
CPC ....... A61B 6/4233; A61B 6/542; A61B 6/545; H05G 1/44; H04N 5/32
See application file for complete search history.

(56) References Cited

U.S. PATENT DOCUMENTS 6,952,015 B2   10/2005   Kameshima
7,227,926 B2    6/2007   Yagi et al.
(Continued)

FOREIGN PATENT DOCUMENTS

CN    1517069 A    8/2004
CN  102934526 A    2/2013
(Continued)

OTHER PUBLICATIONS

U.S. Appl. No. 15/757,693, Katsuro Takenaka, filed Mar. 6, 2018.
U.S. Appl. No. 15/877,694, Hideyuki Okada, filed Jan. 23, 2018.

*Primary Examiner* — Dani Fox
*Assistant Examiner* — Soorena Kefayati
(74) *Attorney, Agent, or Firm* — Venable LLP

(57) ABSTRACT

A radiation imaging system includes a two-dimensional array in which a plurality of elements which detect radiation are two-dimensionally arrayed. The plurality of elements includes a plurality of detectors usable for exposure control of stopping radiation irradiation in accordance with a fact that a radiation irradiation dose has reached a target irradiation dose. The radiation imaging system includes a controller configured to determine, based on a setting of a reading manner of signals from the plurality of detectors, a minimum irradiation time required from the start of radiation irradiation until the stop of radiation irradiation according to signals from the two-dimensional array and perform an error process when the minimum irradiation time exceeds a reference irradiation time.

8 Claims, 17 Drawing Sheets

(51) Int. Cl.
*A61B 6/00* (2006.01)
*H05G 1/44* (2006.01)

(56) References Cited

U.S. PATENT DOCUMENTS

| | | | |
|---|---|---|---|
| 7,342,221 B2 | 3/2008 | Takenaka et al. | |
| 7,381,963 B2 | 6/2008 | Endo et al. | |
| 7,386,089 B2 | 6/2008 | Endo et al. | |
| 7,403,594 B2 | 7/2008 | Yagi et al. | |
| 7,408,167 B2 | 8/2008 | Kameshima et al. | |
| 7,421,063 B2 | 9/2008 | Takenaka et al. | |
| 7,442,939 B2 | 10/2008 | Yagi et al. | |
| 7,466,345 B2 | 12/2008 | Kameshima et al. | |
| 7,476,027 B2 | 1/2009 | Takenaka et al. | |
| 7,491,960 B2 | 2/2009 | Takenaka et al. | |
| 7,514,663 B2 | 4/2009 | Yagi et al. | |
| 7,514,690 B2 | 4/2009 | Endo et al. | |
| 7,532,706 B2 | 5/2009 | Kameshima et al. | |
| 7,541,591 B2 | 6/2009 | Endo et al. | |
| 7,550,733 B2 | 6/2009 | Endo et al. | |
| 7,564,038 B2 | 7/2009 | Endo et al. | |
| 7,573,038 B2 | 8/2009 | Yokoyama et al. | |
| 7,592,599 B2 | 9/2009 | Kameshima | |
| 7,629,587 B2 | 12/2009 | Yagi et al. | |
| 7,645,995 B2 | 1/2010 | Yagi et al. | |
| 7,696,484 B2 | 4/2010 | Yokoyama et al. | |
| 7,718,973 B2 | 5/2010 | Endo et al. | |
| 7,724,874 B2 | 5/2010 | Kameshima et al. | |
| 7,732,776 B2 | 6/2010 | Takenaka et al. | |
| 7,732,778 B2 | 6/2010 | Yokoyama et al. | |
| 7,869,568 B2 | 1/2011 | Yokoyama et al. | |
| 7,965,817 B2 | 6/2011 | Kameshima et al. | |
| 7,989,772 B2 | 8/2011 | Yagi et al. | |
| 8,072,514 B2 | 12/2011 | Takenaka et al. | |
| 8,107,588 B2 | 1/2012 | Kameshima et al. | |
| 8,247,779 B2 | 8/2012 | Kameshima et al. | |
| 8,723,996 B2 | 5/2014 | Yokoyama et al. | |
| 8,755,490 B2 | 6/2014 | Takamura | |
| 8,809,795 B2 | 8/2014 | Takenaka et al. | |
| 8,829,438 B2 | 9/2014 | Sato et al. | |
| 8,873,712 B2* | 10/2014 | Wang | A61B 6/4208 378/97 |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,538,099 B2* | 1/2017 | Kim | H04N 5/3454 |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,750,477 B2* | 9/2017 | Kitagawa | G01T 1/2018 |
| 9,812,474 B2 | 11/2017 | Yagi et al. | |
| 9,885,790 B2 | 2/2018 | Okada et al. | |
| 9,971,046 B2 | 5/2018 | Ryu et al. | |
| 10,022,102 B2* | 7/2018 | Okada | H05G 1/56 |
| 2001/0012330 A1* | 8/2001 | Ogura | A61B 6/588 378/95 |
| 2008/0159481 A1* | 7/2008 | Yoshida | A61B 6/542 378/95 |
| 2008/0317205 A1* | 12/2008 | Inuga | A61B 6/4441 378/97 |
| 2010/0148080 A1 | 6/2010 | Endo et al. | |
| 2011/0317054 A1 | 12/2011 | Kameshima et al. | |
| 2011/0317809 A1* | 12/2011 | Eguchi | A61B 6/566 378/62 |
| 2013/0032696 A1* | 2/2013 | Tajima | H04N 5/361 250/208.1 |
| 2013/0058454 A1* | 3/2013 | Kuwabara | A61B 6/4411 378/62 |
| 2013/0058455 A1* | 3/2013 | Kuwabara | A61B 6/545 378/62 |
| 2013/0058456 A1* | 3/2013 | Kuwabara | A61B 6/4233 378/62 |
| 2013/0121464 A1* | 5/2013 | Tajima | A61B 6/4283 378/62 |
| 2013/0148782 A1* | 6/2013 | Tajima | A61B 6/4233 378/62 |
| 2013/0259196 A1* | 10/2013 | Tajima | A61B 6/4233 378/62 |
| 2013/0272493 A1* | 10/2013 | Otokuni | A61B 6/5205 378/37 |
| 2014/0112448 A1 | 4/2014 | Takenaka et al. | |
| 2014/0239186 A1 | 8/2014 | Sato et al. | |
| 2014/0254760 A1* | 9/2014 | Hiroike | A61B 6/4233 378/62 |
| 2014/0361189 A1 | 12/2014 | Kameshima et al. | |
| 2015/0036802 A1* | 2/2015 | Tajima | A61B 6/4208 378/62 |
| 2015/0055752 A1* | 2/2015 | Takahashi | H04N 5/32 378/62 |
| 2015/0164461 A1* | 6/2015 | Imamura | H05G 1/44 378/97 |
| 2016/0084969 A1 | 3/2016 | Sato et al. | |
| 2017/0079610 A1* | 3/2017 | Morf | A61B 6/4233 |
| 2017/0285189 A1 | 10/2017 | Ryu et al. | |
| 2017/0311920 A1* | 11/2017 | Hiroshige | A61B 6/4452 |
| 2017/0325762 A1* | 11/2017 | Ota | G01T 7/00 |
| 2018/0063933 A1 | 3/2018 | Okada et al. | |
| 2018/0129120 A1 | 5/2018 | Sato et al. | |

FOREIGN PATENT DOCUMENTS

| | | |
|---|---|---|
| CN | 103826538 A | 5/2014 |
| CN | 104124256 A | 10/2014 |
| CN | 104427937 A | 3/2015 |
| JP | 2007-054484 A | 3/2007 |
| JP | 2013-215518 A | 10/2013 |
| JP | 2013-223691 A | 10/2013 |
| JP | 5333580 B | 11/2013 |
| WO | WO2010-116494 A1 | 10/2012 |

* cited by examiner

[Fig. 1]
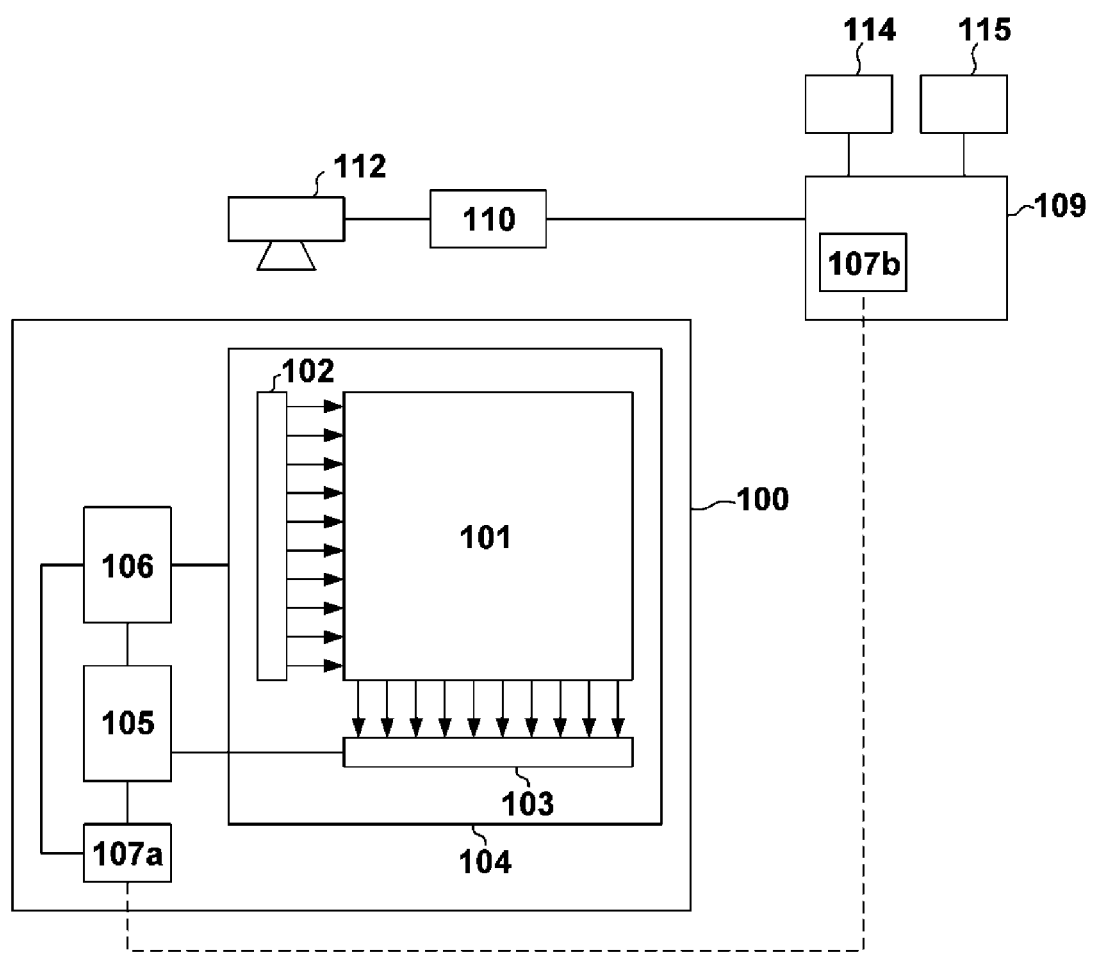

[Fig. 2]
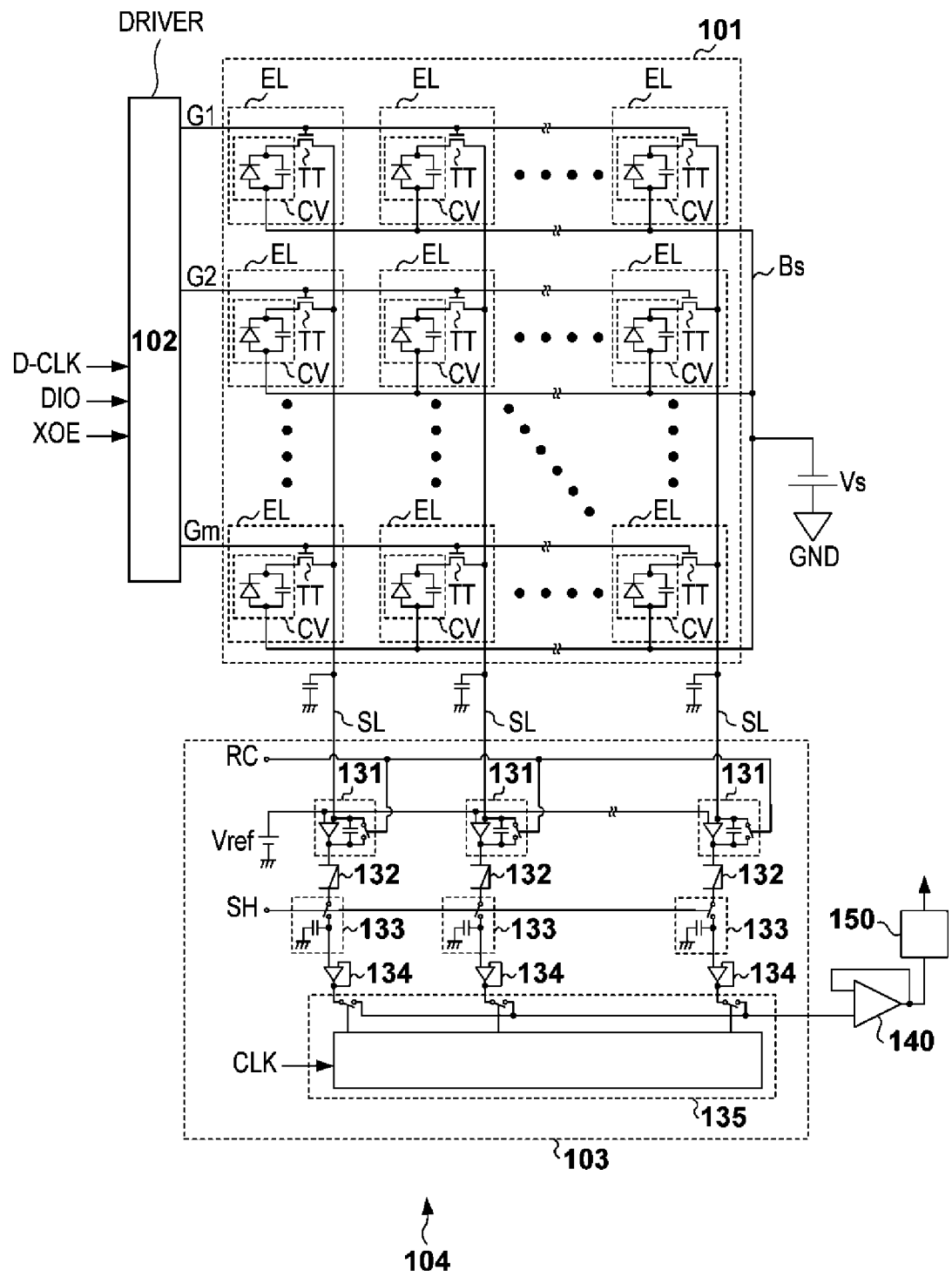

[Fig. 3]
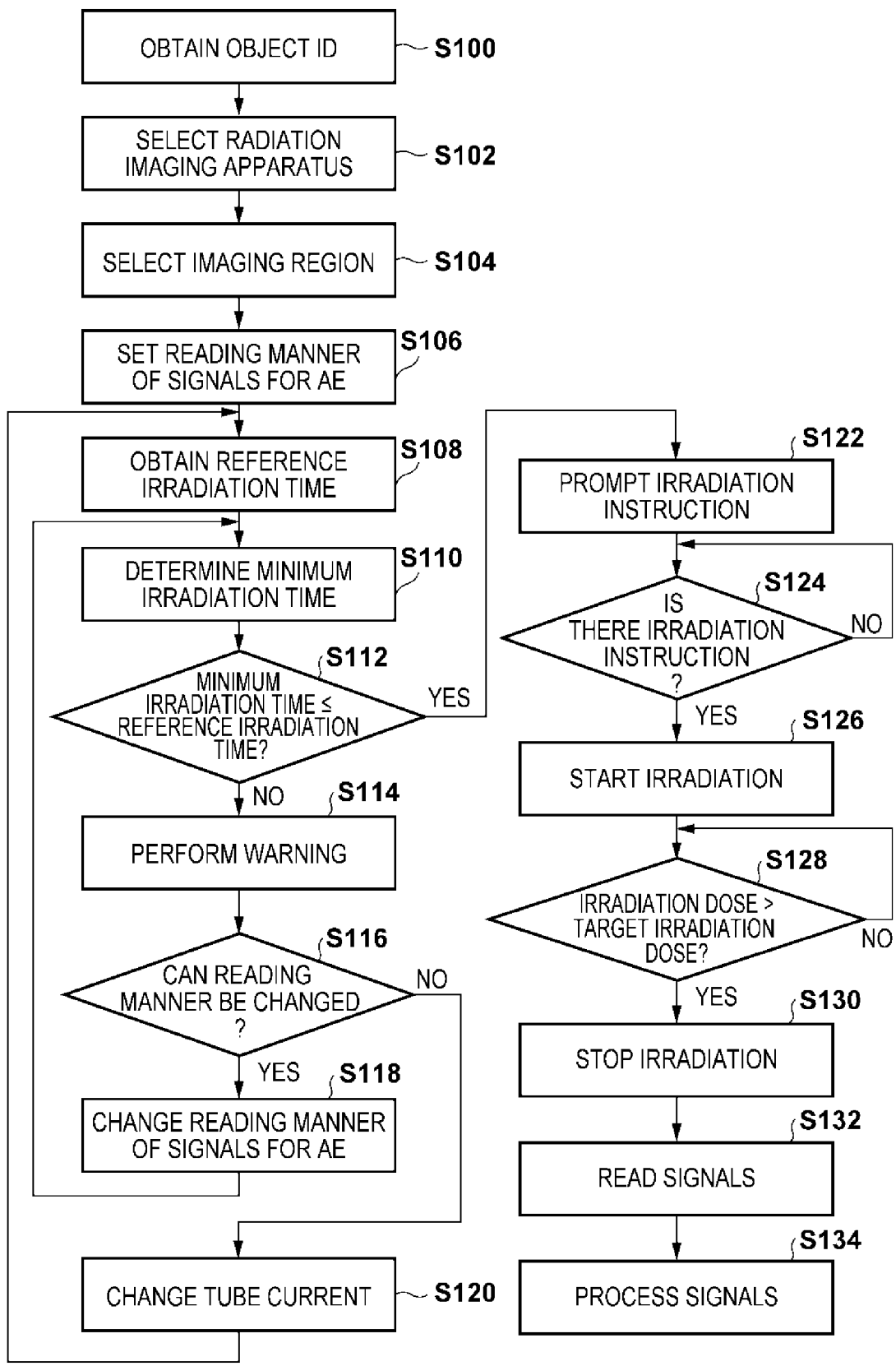

[Fig. 4]

| SELECT | CASSETTE | SIZE | COMMUNI-CATION | COMMUNI-CATION TIME | ONE-ROW READING TIME | NUMBER OF SELECTABLE ROWS | NUMBER OF SIMULTANEOUSLY READABLE ROWS |
|---|---|---|---|---|---|---|---|
| ☒ | C1 | HANSETSU SIZE | WIRELESS | 5ms | 300us | 1-10 | 1 |
| ☐ | C2 | HANSETSU SIZE | WIRELESS | 1ms | 100us | 1-100 | 1-4 |
| ☐ | C3 | 11 x 14 INCHES | WIRELESS | 1ms | 100us | 1-50 | 1-4 |

CASSETTE SELECTION

| SELECT | IMAGING REGION | PHYSICAL SIZE | TUBE VOLTAGE | TUBE CURRENT | REFERENCE IRRADIATION TIME |
|---|---|---|---|---|---|
| ☑ | CHEST REGION | STANDARD | ○kVp | ●mA | 50ms |
| ☐ | ABDOMINAL REGION | STANDARD | △kVp | ▲mA | 70ms |
| ☐ | LUMBAR VERTEBRA REGION | STANDARD | □kVp | ■mA | 150ms |

IMAGING REGION SELECTION

114

[Fig. 6]
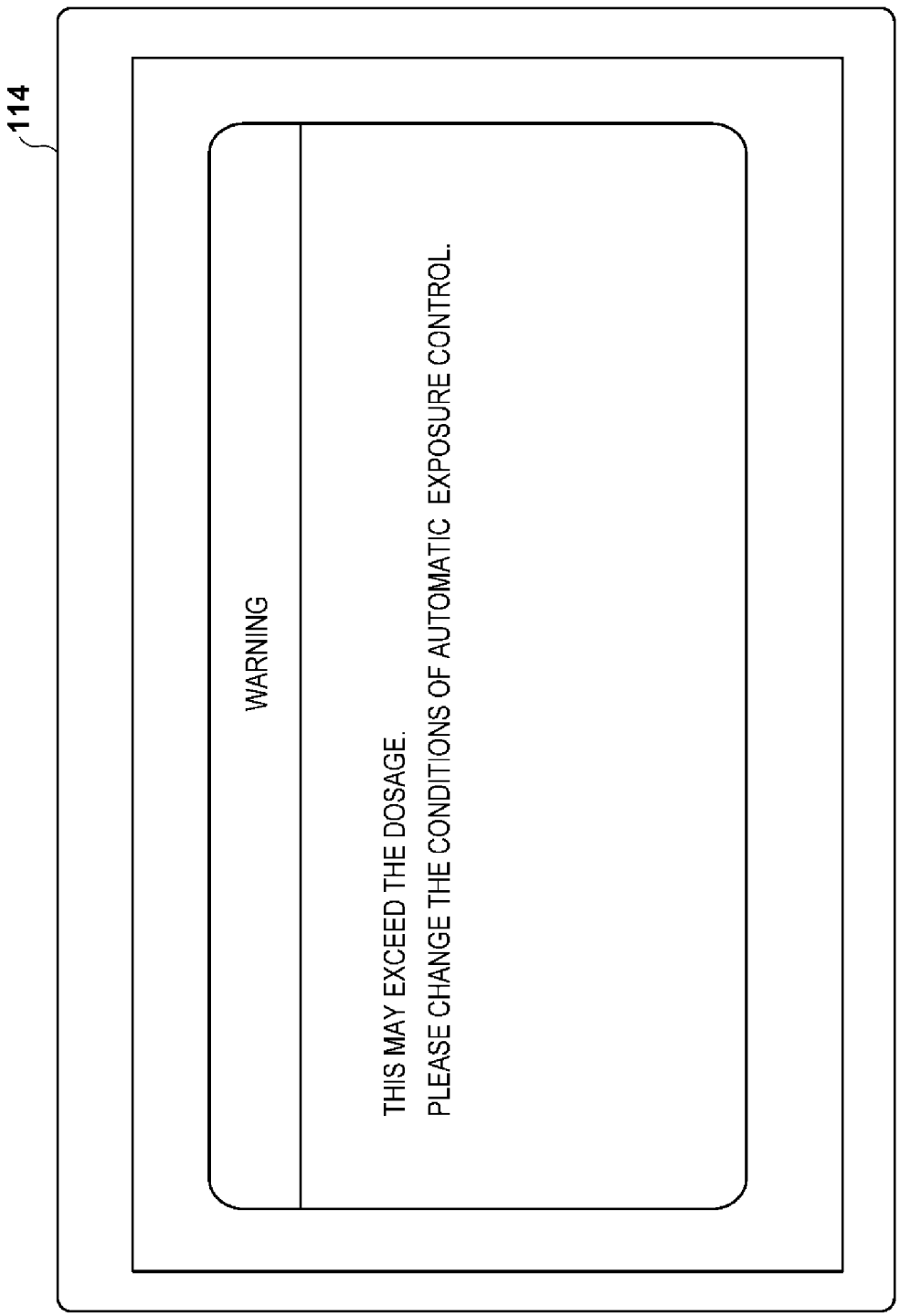

[Fig. 7]

SETTING OF AUTOMATIC EXPOSURE CONTROL

PLEASE CHANGE THE CONDITIONS OF AUTOMATIC EXPOSURE CONTROL.

| CASSETTE | SIZE | COMMUNI-CATION | NUMBER OF ROWS FOR READING | NUMBER OF ROWS FOR SIMULTANEOUS READING |
|---|---|---|---|---|
| C1 | HANSETSU SIZE | WIRELESS | 10 | 1 |

114

[Fig. 8]
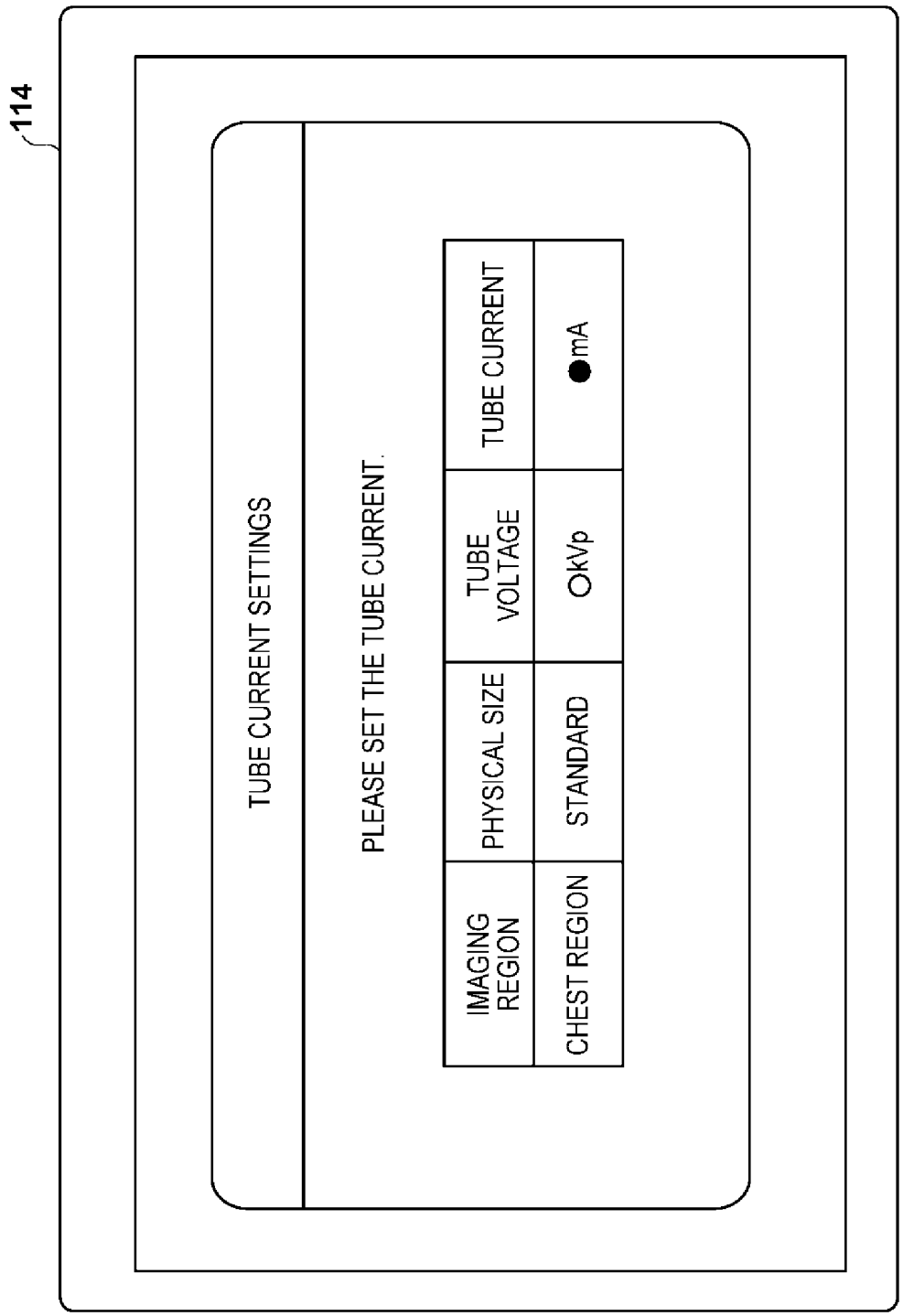

[Fig. 9A]
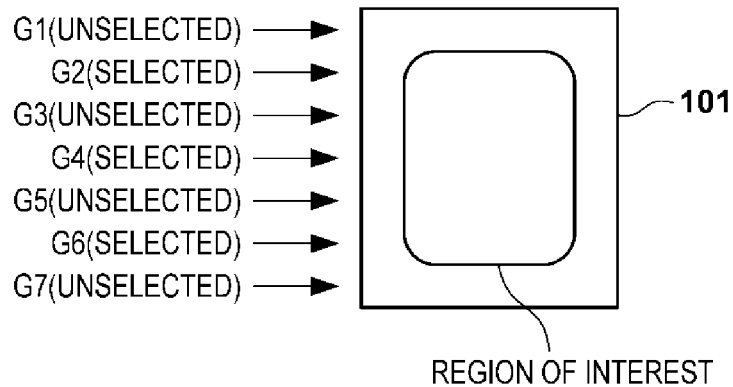
[Fig. 9B]
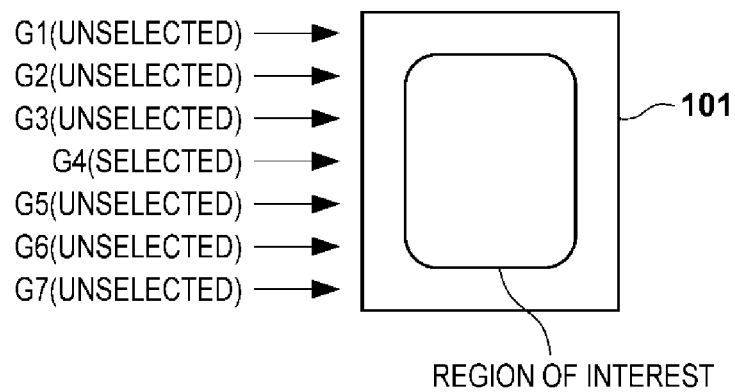
[Fig. 9C]
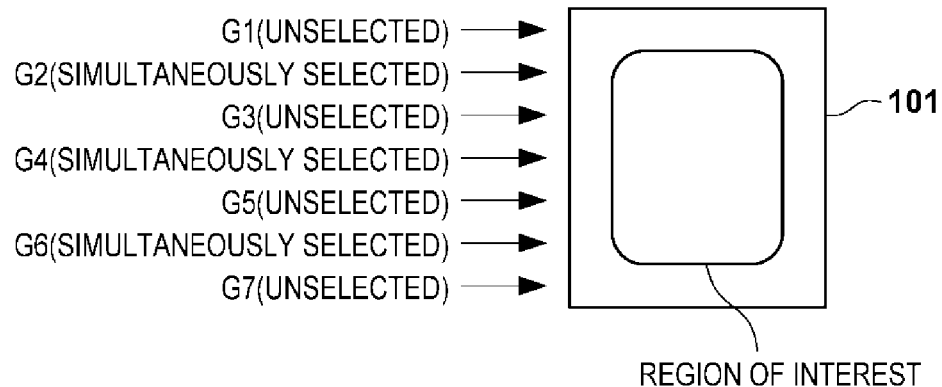

[Fig. 10]
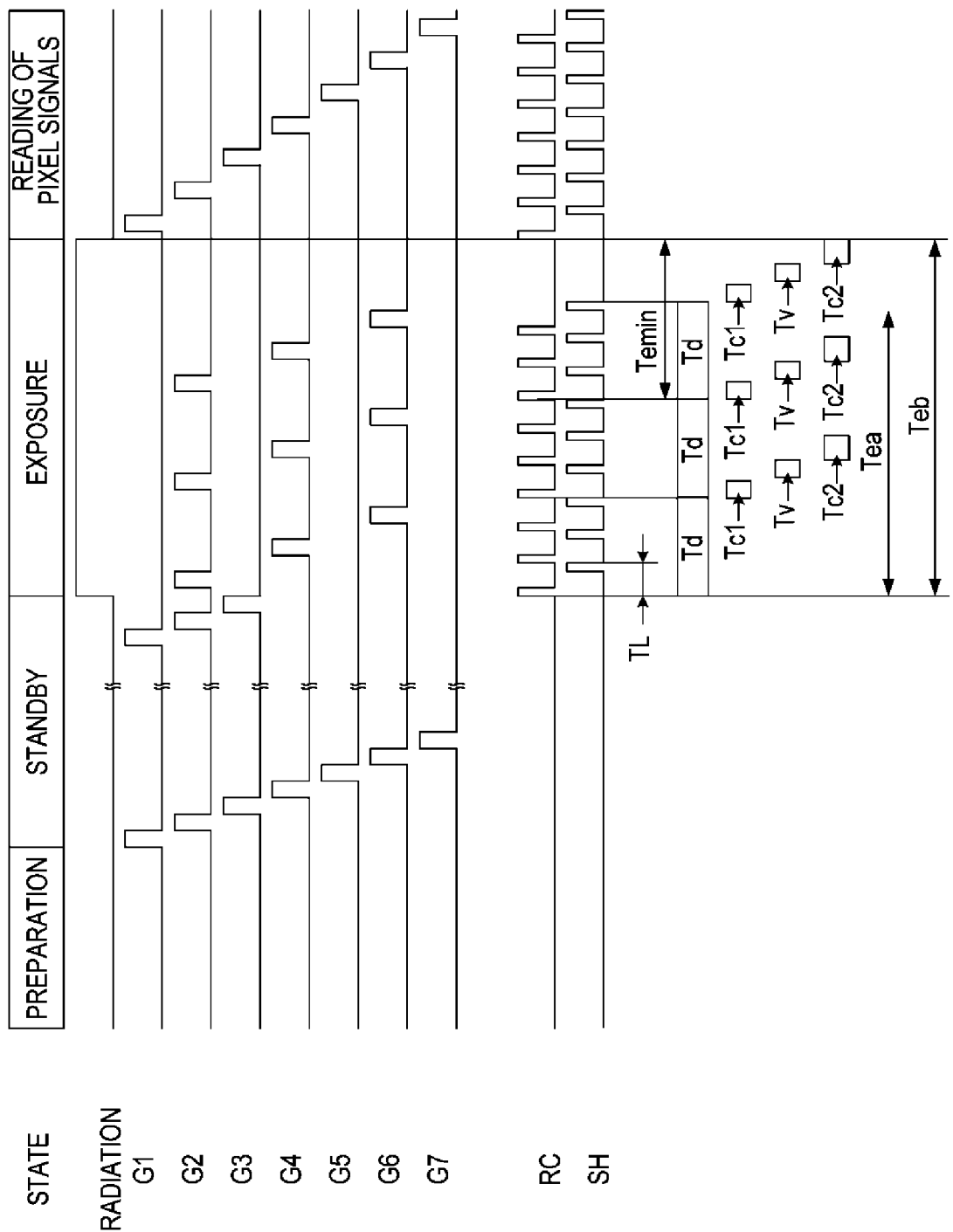

[Fig. 11]
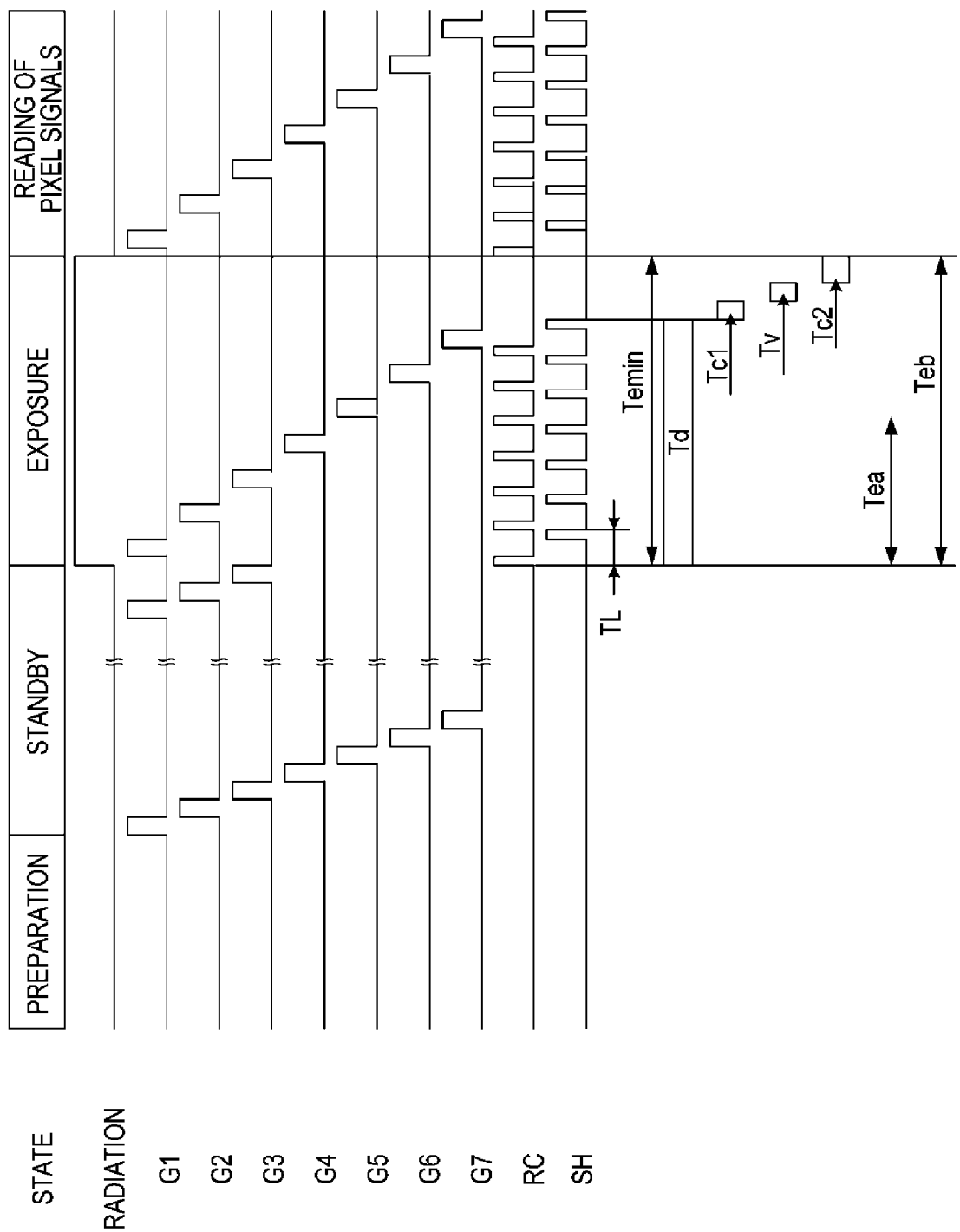

[Fig. 12]
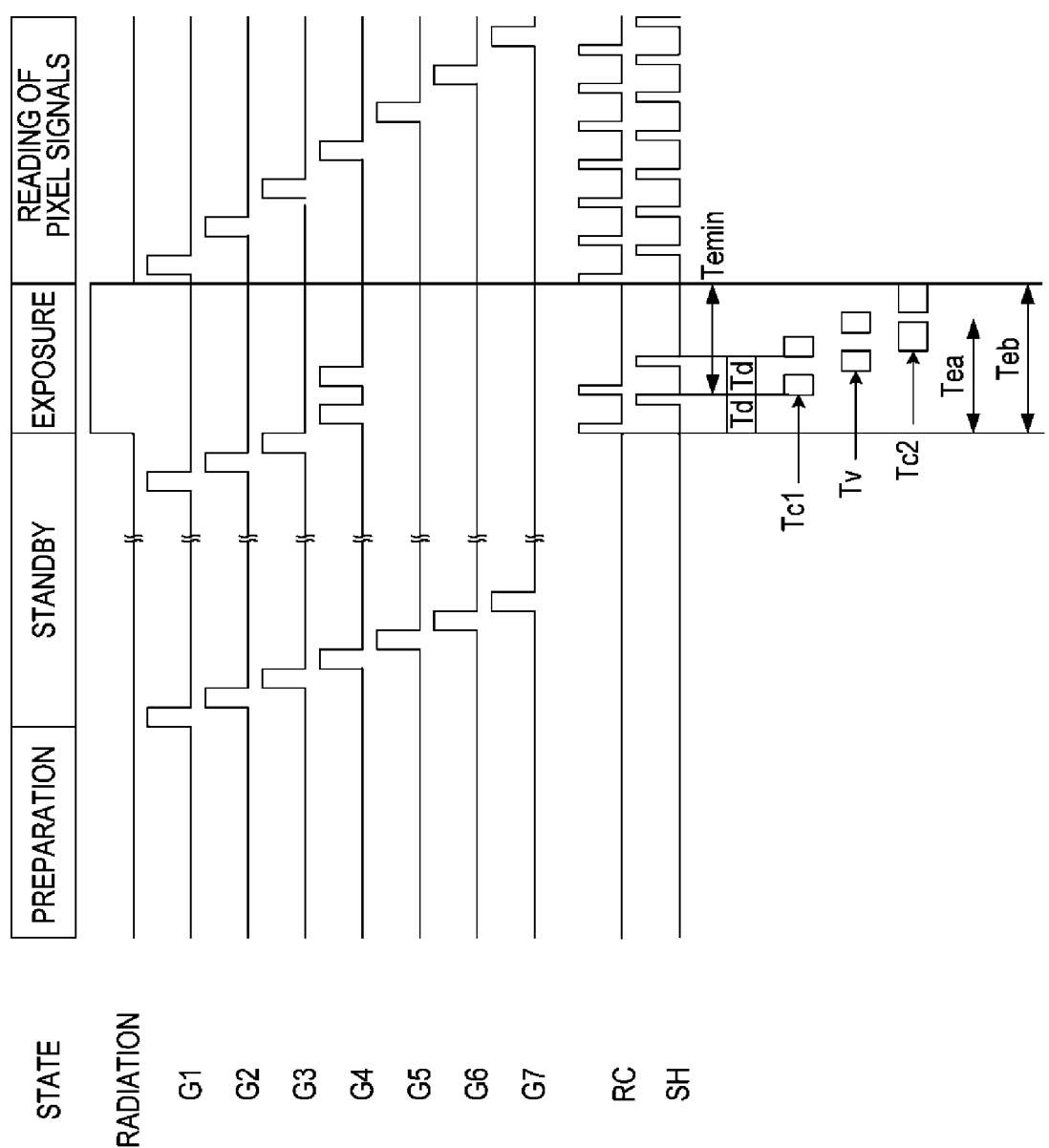

[Fig. 13]
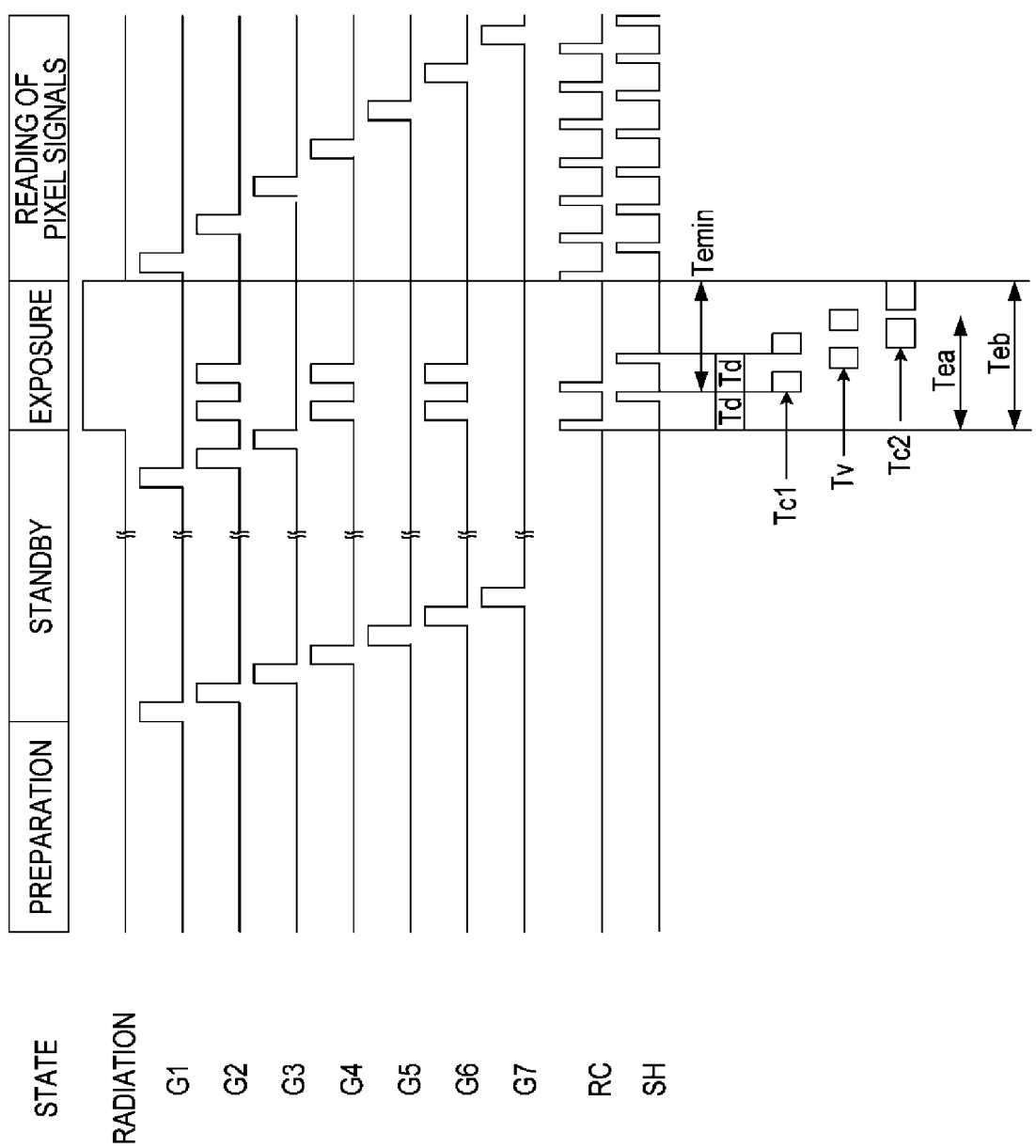

[Fig. 14A]
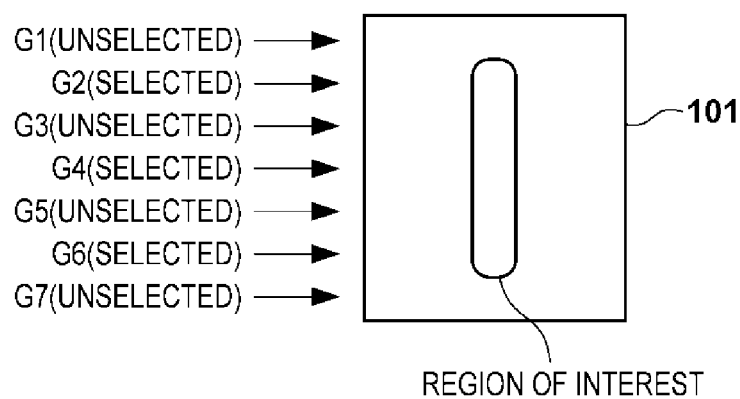
[Fig. 14B]
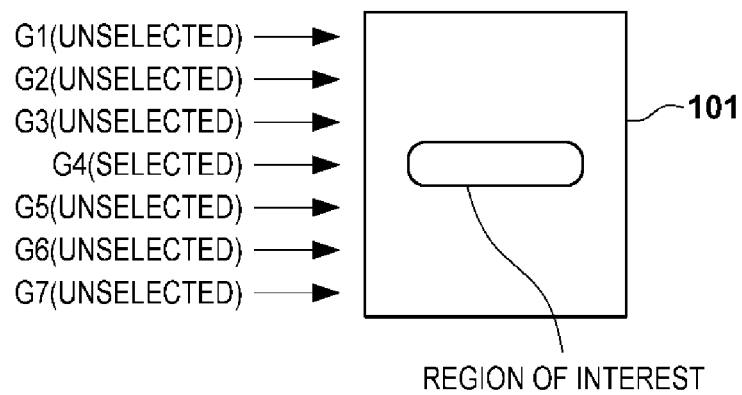

[Fig. 15]
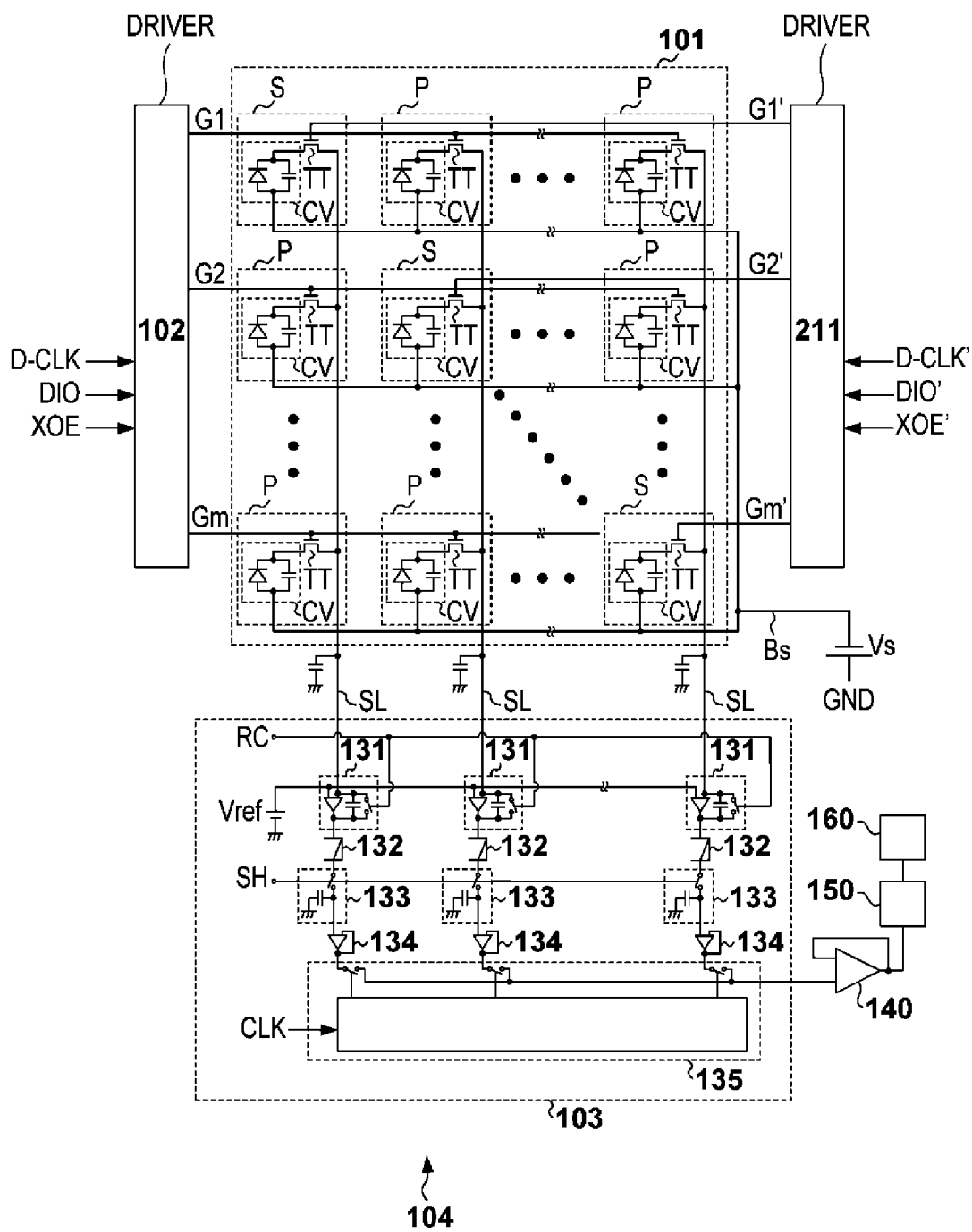

[Fig. 16A]
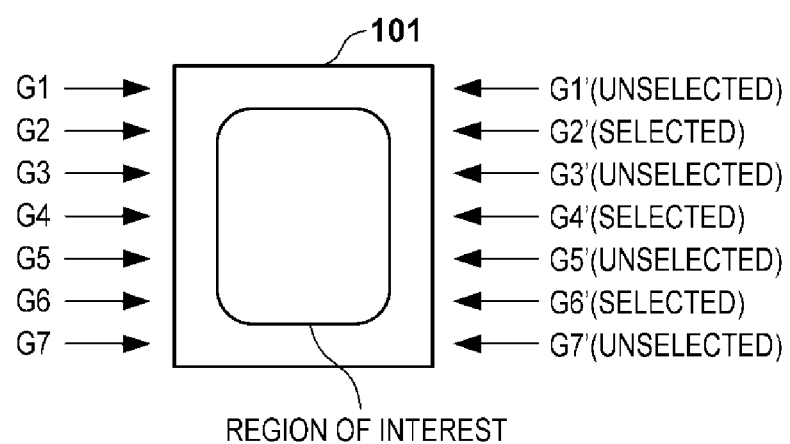
[Fig. 16B]
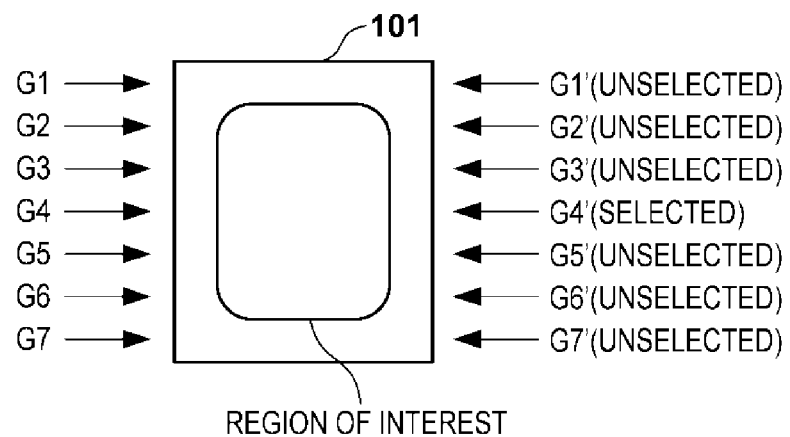

[Fig. 17]
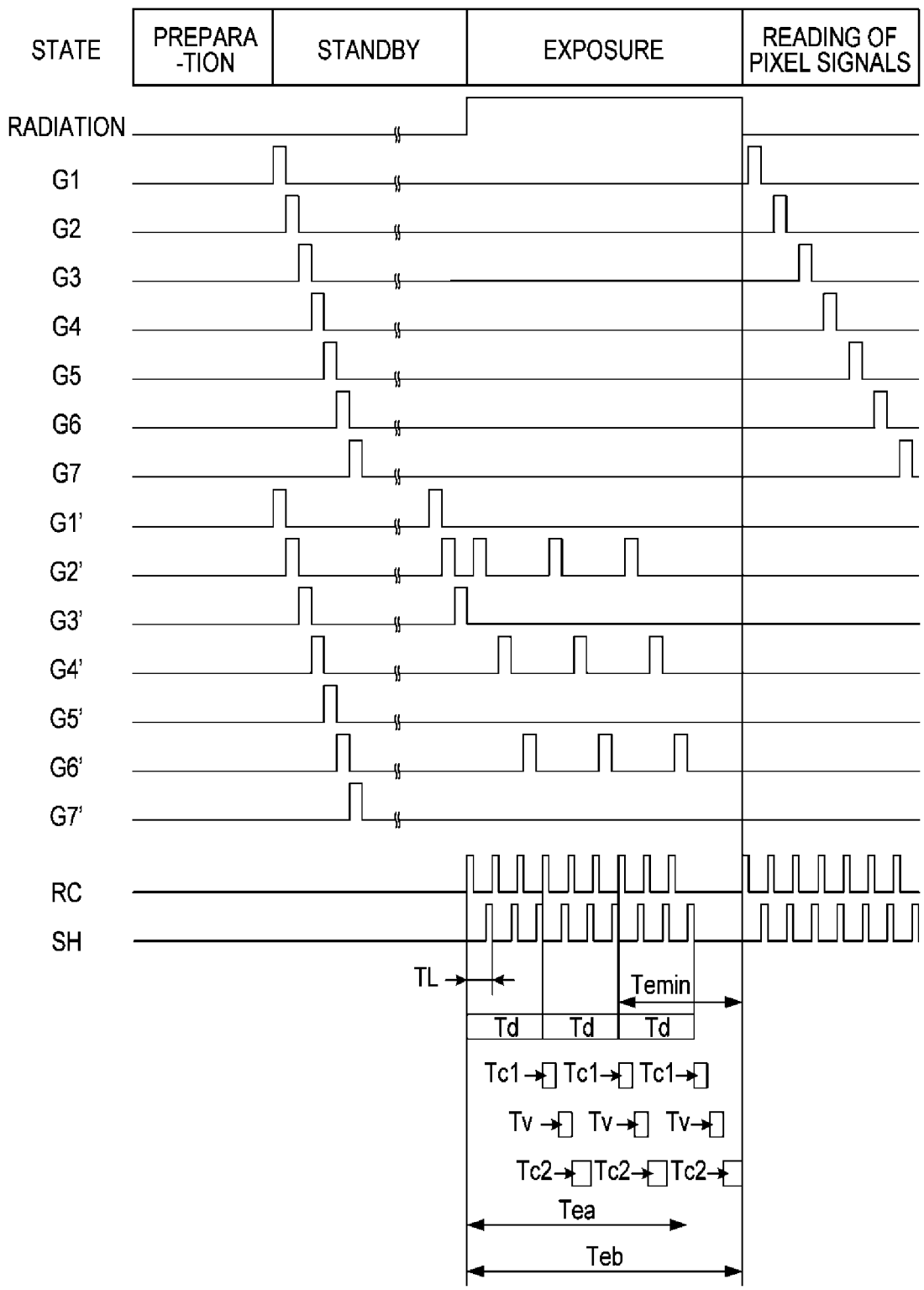

RADIATION IMAGING SYSTEM

TECHNICAL FIELD

The present invention relates to a radiation imaging system.

BACKGROUND ART

There is known a radiation imaging system that includes a radiation imaging apparatus for electrically capturing an image formed by radiation. The radiation imaging system can have an automatic exposure function which detects that the radiation dose emitted from the radiation source to the radiation imaging apparatus has reached a predetermined irradiation dose and stops the radiation irradiation from the radiation source based on this detection. Excessive radiation irradiation to an object caused by an inability to detect that the radiation irradiation dose has reached a predetermined irradiation dose must be avoided in an automatic exposure function.

Japanese Patent No. 5333580 relates to an X-ray imaging apparatus. In Japanese Patent No. 5333580, a warning is generated when a backup time set as an X-ray exposure limit time in an X-ray controller is shorter than an imaging time obtained from the thickness of an object and the X-ray conditions.

Japanese Patent Laid-Open No. 2013-215518 relates to a radiation imaging system. In Japanese Patent Laid-Open No. 2013-215518, when a necessary minimum irradiation time from when the radiation irradiation is started until the radiation irradiation is stopped by an automatic exposure control means is longer than a predetermined irradiation time, a tube current is corrected so that the actual radiation irradiation time becomes equal to or more than the minimum irradiation time.

In the technique described in Japanese Patent Laid-Open No. 2013-215518, excessive radiation irradiation to an object can be prevented by correcting the tube current. However, the image quality of the obtained radiation image can degrade when the intensity of the radiation is reduced by decreasing the tube current. In addition, the manner of correcting the tube current requires a radiation source which supports such a function and an exposure controller for controlling such a function.

SUMMARY OF INVENTION

The present invention provides a technique advantageous in suppressing image quality reduction of a radiation image and avoiding excessive radiation irradiation.

One of aspects of the present invention provides a radiation imaging system that includes a two-dimensional array in which a plurality of elements which detect radiation are two-dimensionally arrayed, the plurality of elements including a plurality of detectors usable for exposure control of stopping radiation irradiation in accordance with a fact that a radiation irradiation dose has reached a target irradiation dose, and the radiation imaging system includes a controller configured to determine, based on a setting of a reading manner of signals from the plurality of detectors, a minimum irradiation time required from the start of radiation irradiation until the stop of radiation irradiation according to signals from the two-dimensional array and perform an error process when the minimum irradiation time exceeds a reference irradiation time.

Further features of the present invention will become apparent from the following description of exemplary embodiments with reference to the attached drawings.

BRIEF DESCRIPTION OF DRAWINGS

FIG. 1 is a block diagram showing the arrangement of a radiation imaging system according to the first embodiment;
FIG. 2 is a diagram showing the arrangement of an imaging device in a radiation imaging apparatus of the radiation imaging system according to the first embodiment;
FIG. 3 is a flowchart showing the operation of the radiation imaging system according to the first embodiment;
FIG. 4 is a view exemplifying a cassette selection screen;
FIG. 5 is a view exemplifying an imaging region selection screen;
FIG. 6 is a view exemplifying a warning display;
FIG. 7 is a view exemplifying an automatic exposure control setting screen;
FIG. 8 is a view exemplifying a tube current setting screen;
FIG. 9A is a view exemplifying a signal reading manner for exposure control;
FIG. 9B is a view exemplifying another signal reading manner for exposure control;
FIG. 9C is a view exemplifying yet another signal reading manner for exposure control;
FIG. 10 is a timing chart showing an operation example of the reading manner of FIG. 9A;
FIG. 11 is a timing chart showing an example in which a minimum irradiation time Temin exceeds a reference irradiation time Tea;
FIG. 12 is a timing chart showing an operation example of the reading manner of FIG. 9B;
FIG. 13 is a timing chart showing an operation example of the reading manner of FIG. 9C;
FIG. 14A is a view exemplifying a signal reading manner for exposure control;
FIG. 14B is a view exemplifying another signal reading manner for exposure control;
FIG. 15 is a diagram showing the arrangement of an imaging device in a radiation imaging apparatus of a radiation imaging system according to the second embodiment;
FIG. 16A is a view exemplifying a signal reading manner for exposure control according to the second embodiment;
FIG. 16B is a view exemplifying another signal reading manner for exposure control according to the second embodiment; and
FIG. 17 is a timing chart showing an operation example of the reading manner of FIG. 16A.

DESCRIPTION OF EMBODIMENTS

The present invention will be described below by way of exemplary embodiments.

FIG. 1 shows the arrangement of a radiation imaging system DRS according to the first embodiment of the present invention. The radiation imaging system DRS includes a radiation imaging apparatus 100 and detects, as an electrical image signal, an image formed from radiation that has been emitted from a radiation source 112 and passed through an object. The concept of radiation includes, for example, a-rays, n-rays, grays, and the like.

The radiation imaging system DRS further includes a radiation source 112, a main controller (controller) 109, and an exposure controller 110. The radiation source 112 emits radiation. Other than controlling the radiation imaging apparatus 100, the main controller 109 controls the radiation source 112 via the exposure controller 110. All or some of the functions of the main controller 109 may be incorporated in, for example, the radiation imaging apparatus 100 or the exposure controller 110. All or some of the functions of the exposure controller 110 may be incorporated in, for example, the main controller or the radiation imaging apparatus 100. The main controller 109 may include a display 114 and an input device 115.

The radiation imaging apparatus 100 can include an imaging device 104, a signal processor 105, an imaging controller 106, and a communication device 107a. The imaging device 104 includes a two-dimensional array 101 in which a plurality of elements which detect radiation are two-dimensionally arrayed so as to form a plurality of rows and a plurality of columns, a driver 102 which drives the two-dimensional array 101, and a reader 103 which reads signals from the two-dimensional array 101. The signal processor 105 processes a signal output from the imaging device 104. The imaging controller 106 controls the imaging device 104, the signal processor 105, and the communication device 107a. The communication device 107a communicates with a communication device 107b provided in the main controller 109 using wired or wireless communication. That is, the radiation imaging apparatus 100 and the main controller 109 communicate with each other via the communication devices 107a and 107b.

FIG. 2 shows an example of the arrangement of the imaging device 104. The imaging device 104 can include, as described above, the two-dimensional array 101, the driver 102 which drives the two-dimensional array 101, and the reader 103 which reads signals from the two-dimensional array 101. The two-dimensional array 101 has an arrangement in which a plurality of elements EL that detect radiation are two-dimensionally arrayed so as to form a plurality of rows and a plurality of columns. The plurality of elements EL include a plurality of detectors usable for exposure control to stop radiation irradiation in accordance with the fact that the radiation irradiation dose has reached a target irradiation dose.

In the first embodiment, each element EL is a pixel that captures a radiation image and is also a detector usable for exposure control of stopping radiation irradiation in accordance with the fact that the radiation irradiation dose has reached a target irradiation dose. Each element (pixel) EL includes a conversion element CV that converts radiation or light into charges and a switch element TT that outputs an electric signal corresponding to the charges generated by the conversion element CV.

Each conversion element CV converts radiation into charges. Each conversion element CV can be constituted by a scintillator which converts radiation into visible light and a photoelectric conversion element which converts visible light into the charges. In this case, the plurality of conversion elements CV can share the scintillator. Each conversion element CV may be configured to directly convert radiation into the charges. Each conversion element CV can be constituted by a MIS or a PIN photoelectric conversion element. Each switch TT can be constituted by, for example, a thinfilm transistor (TFT). The switch TT connects the first electrode of each conversion element CV and a corresponding signal line SL in accordance with a driving signal G (the corresponding signal out of the driving signals G1, G2, G3 . . . Gm). The second electrode of each conversion element CV is connected to a bias corresponding line Bs. The bias voltage Vs is supplied to each bias line Bs. Here, Gn (n=1 to m) indicates the driving signal that drives (the switch TT of) the nth row elements EL.

When the nth row driving signal Gn is driven to active level by the driver 102, the switch TT of each nth row element (pixel) is turned on (becomes conductive), and the charges accumulated in the conversion element CV of the element EL are transferred to the corresponding signal line SL through the switch TT. That is, when the nth row driving signal Gn is driven to active level by the driver 102, the signal of each nth row element EL is output to the corresponding signal line SL. Note that, although the active level is high level in this embodiment, the active level may also be set to low level.

The reader 103 reads the signals from the elements EL via the signal lines SL. The reader 103 includes, for each column in the two-dimensional array 101, an integrating amplifier 131, a variable amplifier 132, a sample and hold circuit 133, and a buffer amplifier 134. The signal output to each signal line SL is amplified by the integrating amplifier 131 and the variable amplifier 132, is sampled and held by the sample and hold circuit 133, and is amplified by the buffer amplifier 134. The reader 103 includes a multiplexer 135. The signal output from the buffer amplifier 134 provided for each column is selected by the multiplexer 135 and output to an amplification device 140. The output from the amplification device 140 is AD-converted by an AD converter 150 and output to the signal processor 105.

Each integrating amplifier 131 includes an operational amplifier, an integral capacitor, and a reset switch. The signal output to each signal line SL is input to the inverting input terminal of the operational amplifier, a reference voltage Vref is input to the non-inverting input terminal, and the amplified signal is output from the output terminal. The integral capacitor is arranged between the inverting input terminal and the output terminal of the operational amplifier. Each variable amplifier 132 amplifies the signal from the corresponding integrating amplifier 131 at an amplification factor designated by the imaging controller 106. Each sample and hold circuit 133 can be formed from a sampling switch and a sampling capacitor.

The reset switch of each integrating amplifier 131 is controlled to be ON (conductive) or OFF (non-conductive) by a control signal (reset signal) RC. The sampling switch of each sample and hold circuit 133 is controlled to be ON or OFF by the control signal (sampling signal) SH. The multiplexer 135 selects, in accordance with a control signal CLK, each signal read from the two-dimensional array 101 via the plurality of signal lines SL.

The driver 102 generates, in accordance with control signals (D-CLK, DIO, XOE) supplied from the imaging controller 106, the driving signal G for controlling, for each row, the switches TT of the respective elements EL in the two-dimensional array 101. The driver 102 includes a shift register, and the control signal D-CLK is a clock signal supplied as a shift clock to the shift register. The control signal DIO is a shift pulse supplied to the shift register, and the control signal XOE is an output enable signal to the shift register. Although the driver 102 is formed by a shift register in this example, the driver 102 may also be formed by a circuit capable of random access.

The operation of the radiation imaging system DRS will be described below with reference to FIG. 3. This operation can be controlled by the main controller 109. The main controller 109 can be, for example, formed by a general purpose or a dedicated computer which has a CPU and a memory. A computer program for controlling the CPU is stored in the memory, and the CPU operates in accordance with the computer program.

First, in step S100, the main controller 109 obtains an object ID via the input device 115 (not shown). The main controller 109 can obtain preregistered object information (for example, physical size information such as the weight, past imaging conditions, and the like) based on the object ID.

Next, in step S102, the main controller 109 selects, out of the plurality of radiation imaging apparatuses 100 which can be used, one radiation imaging apparatus 100 in accordance with the information provided by the operator. Here, for the sake of descriptive convenience, assume that the radiation imaging apparatus 100 is in the form of a cassette. Hence, the radiation imaging apparatus 100 will also be described as a cassette. A cassette selection screen is exemplified in FIG. 4. This selection screen is displayed on the display 114, and the operator can operate the input device 115 to select the cassette to be used out of a plurality of cassettes C1 to C3. A hansetsu size cassette C1 has been selected in the example shown in FIG. 4.

Next, in step S104, the main controller 109 selects the imaging region according to the information provided by the operator. An imaging region selection screen is exemplified in FIG. 5. This selection screen is displayed on the display 114, and the operator can select the imaging region by operating the input device 115. Imaging of the chest region has been selected in the example shown in FIG. 5. A reference irradiation time is associated with each imaging region.

Next, in step S106, the main controller 109 sets the reading manner for reading the signals from the two-dimensional array 101 for exposure control (AE) based on, for example, the imaging region and the radiation imaging apparatus (cassette) 100 to be used. Here, exposure control is control performed by the main controller 109 to stop radiation irradiation by the radiation source 112 in accordance with the fact that the radiation irradiation dose has reached the target irradiation dose. Radiation irradiation is stopped when the main controller 109 transmits a stop command to the exposure controller 110. Upon receiving the stop command, the exposure controller 110 causes the radiation source 112 to stop radiation irradiation.

If object information such as the physical size information of the object and the like can be obtained based on the object ID obtained in step S100, the signal reading manner can be set based on the object information in addition to the imaging region and the radiation imaging apparatus 100 to be used. Alternatively, the signal reading manner can be set based on at least one of the radiation imaging apparatus 100 to be used, the imaging region, and the object information. Alternatively, a default reading manner may be set regardless of the radiation imaging apparatus 100 to be used, the imaging region, and the object information.

As described above, in the first embodiment, each element EL is a pixel that captures a radiation image and is also a detector usable for exposure control of stopping radiation irradiation in accordance with the fact that the radiation irradiation dose has reached a target irradiation dose.

The setting of the reading manner of the signals from the two-dimensional array 101 can include the designation of at least one element EL (detector), out of the plurality elements EL (detectors), which is to be used for exposure control. The designation of at least one element EL (detector) for exposure control may also be performed by designating at least one row out of the plurality of rows forming the two-dimensional array 101. Here, each row of the plurality of rows includes one of the plurality of elements (detectors) forming the two-dimensional array 101. Each element EL (detector) that belongs to at least one row designated for exposure control can be designated as the at least one element EL (detector) for exposure control. The designation of at least one element EL (detector) for exposure control may also be performed by designating a region of interest in the two-dimensional array 101 and designating at least one row. In this case, each element EL (detector) belonging to the designated region of interest and belonging to the at least one row can be designated as the at least one element EL (detector) for exposure control.

Alternatively, the reading manner of the signals from the two-dimensional array 101 can be set by designating at least two rows out of the plurality of rows forming the two-dimensional array 101 as the reading target rows for exposure control. In this case, the setting of the reading manner of the signals from the two-dimensional array 101 can include the number of rows to perform simultaneous reading of signals from the elements EL (detectors) belonging to at least two rows selected for exposure control.

Alternatively, the at least one element EL (detector) for exposure control can be designated by designating a region of interest in the two-dimensional array 101. In this case, each element EL (detector) belonging to the designated region of interest can be designated as the at least one element EL (detector) for exposure control.

In FIG. 4, the selectable number of rows represents the number of rows usable for exposure control out of the plurality of rows formed by the plurality of elements EL (detectors) forming the two-dimensional array 101. For example, if the radiation imaging apparatus 100 as the cassette C1 is to be used, the number of rows usable for exposure control is 1 to 10. In FIG. 4, the number of rows capable of simultaneous reading represents the number of rows that can perform simultaneous reading of signals from the elements EL (detectors) for exposure control. For example, if the radiation imaging apparatus 100 as the cassette C1 is to be used, the number of rows capable of simultaneous reading of signals from the elements EL (detectors) for exposure control is 1. This represents that the signals cannot be simultaneously read from the elements EL (detectors) of a plurality of rows. For example, if the radiation imaging apparatus 100 as the cassette C2 is to be used, the number of rows capable of simultaneous reading of signals from the elements EL (detectors) for exposure control is 1 to 4.

Next, in step S108, the main controller 109 obtains the reference irradiation time Tea associated with the imaging region obtained in step S104. The reference irradiation time Tea can be, for example, the standard radiation irradiation time when an object having a standard physical size is to be imaged or a time obtained by adding a positive or negative margin to the irradiation time. If object information such as the physical size information of the object and the like can be obtained based on the object ID obtained in step S100, the main controller 109 can obtain the reference irradiation time based on the radiation imaging apparatus (cassette) 100 to be used, the imaging region, and the object information. Alternatively, the main controller 109 may determine the reference irradiation time based on the irradiation time of a past imaging operation of the object.

Next, in step S110, the main controller 109 determines, based on the reading manner setting made in step S106, the minimum irradiation time Temin required from the start of radiation irradiation until the radiation irradiation is stopped in accordance with the signals from the two-dimensional array 101. In one example, the minimum irradiation time Temin is determined in accordance with the arrangement of the radiation imaging system and can be given by $$Temin = Td + Tc1 + Tv + Tc2 \quad (1)$$

where Td is a reading time required for reading all of the signals of the elements EL (detectors) for exposure control as detection signals. Tc1 is a communication time required for transmitting the detection signals from the radiation imaging apparatus (cassette) 100 to be used to the main controller 109 and depends on the radiation imaging apparatus (cassette) 100. Tc1 is exemplified as "communication time" in FIG. 4. Tv is a time required for the main controller 109 to determine whether the integrated value (that is, the radiation irradiation dose) of the detection signals has reached the threshold (target irradiation dose) and is held by the main controller 109 in advance. Tc2 is a delay time required for the radiation source 112 to stop radiation irradiation after the main controller 109 transmits a stop command to the exposure controller 110 and is held by the main controller 109 in advance.

In one example, the reading time Td is calculated by $$Td = TL \times L \div S \quad (2)$$

where TL is a one-row reading time required for reading the signals of one row of elements EL (detectors) for exposure control as detection signals. TL is exemplified as "one-row reading time" in FIG. 4. L is the number of rows in which signals are read from the two-dimensional array 101 for exposure control. L is specified by the reading manner set in step S106. In particular, L is the number of rows designated as reading target rows for exposure control in the reading manner set in step S106. L is designated in the row number range exemplified as "selectable number of rows" in FIG. 4. S is the number of rows in which signals are simultaneously read from the two-dimensional array 101 for exposure control. S is specified by the reading manner set in step S106. In particular, S is the number of rows designated as rows to perform simultaneous reading of signals in the reading manner set in step S106. S is designated in the row number range exemplified as "simultaneously readable number of rows" in FIG. 4.

The minimum irradiation time Temin is determined by changeable parameters L and S. That is, the minimum irradiation time Temin can be changed by changing at least one of L and S.

In step S112, the main controller 109 determines whether the minimum irradiation time Temin is equal to or less than the reference irradiation time Tea. If the minimum irradiation time Temin is not equal to or less than the reference irradiation time Tea, the error process in steps S114 to S120 is executed. On the other hand, if the minimum irradiation time Temin is equal to or less than the reference irradiation time Tea, the main controller 109 executes the imaging process in steps S122 to S134. The fact that the minimum irradiation time Temin is not equal to or less than the reference irradiation time Tea indicates that the exposure control accuracy is low if imaging is executed in accordance with the current reading manner settings. On the other hand, the fact that the minimum irradiation time Temin is equal to or less than the reference irradiation time Tea indicates that the exposure control accuracy is high if imaging is executed in accordance with the current reading manner settings.

If the minimum irradiation time Temin is not equal to or less than the reference irradiation time Tea, the main controller 109 executes the error process in steps S114 to S120 as described above. The main controller 109 first executes a warning process to generate a warning in step S114. The warning can be performed, for example, by using the display 114. FIG. 6 exemplifies the warning (warning display) performed by using the display 114. Furthermore, in step S116, the main controller 109 determines whether the signal reading manner for exposure control can be changed. If changeable, step S118 is executed. Otherwise, step S120 is executed.

In step S118, the main controller 109 changes the signal reading manner for exposure control. The changing of the reading manner may be performed automatically so that the minimum irradiation time Temin will not exceed the reference irradiation time Tea or be performed based on the information provided by the operator. The former manner can be performed by, for example, the main controller 109 decreasing the number L of rows in which the signals are read from the two-dimensional array 101 for exposure control and/or increasing the number S of rows in which the signals are simultaneously read from the two-dimensional array 101 for exposure control.

The latter manner will be described below. The main controller 109 displays the automatic exposure control setting screen exemplified in FIG. 7 on the display 114 and prompts the operator to change L indicated as "number of rows for reading" and/or S indicated as "number of rows for simultaneous reading". The main controller 109 changes L and/or S based on the information provided by the operator. The main controller 109 subsequently returns to step S110 and repeats the subsequent processes.

In step S120, the main controller 109 changes the tube current (more specifically, decreases the tube current) of the radiation source 112. In particular, the main controller 109 displays the tube current setting screen exemplified in FIG. 8 on the display 114, prompts the operator to change the tube current, and changes the tube current based on the information provided by the operator. The main controller 109 subsequently returns to step S108 and repeats the subsequent processes. Note that step S120 is omitted in an arrangement in which the radiation source 112 does not include a function to change the tube current. In addition, if the relation Temin≤Tea cannot be implemented due to the change in the reading manner or the change in the tube current, a warning indicating this state can be made.

In step S112, if the main controller 109 determines that the minimum irradiation time Temin is equal to or less than the reference irradiation time Tea, the main controller 109 executes the imaging process in steps S122 to S134. First, in step S122, the main controller 109 prompts the operator to input a radiation irradiation instruction via the display 114. In step S124, the main controller 109 waits to receive a radiation irradiation instruction from the operator. Upon receiving the radiation irradiation instruction from the operator, the main controller 109 transmits a radiation irradiation command to the exposure controller 110 in step S126. In response, the exposure controller 110 controls the radiation source 112 to start radiation irradiation, and radiation irradiation from the radiation source 112 is started. Note that in a form in which the exposure controller 110 includes an exposure switch, the exposure controller 110 controls the radiation source 112 to start the emission of radiation in response to the operation of the exposure switch and notifies the main controller 109 that the radiation irradiation will be started.

When the radiation irradiation is started, the main controller 109 notifies the radiation imaging apparatus 100 of the start and causes the radiation imaging apparatus 100 to start imaging (accumulate charges in accordance with the incident radiation dose). Upon start of the imaging, the radiation imaging apparatus 100 reads the signals of the elements EL (detectors) for exposure control from the two-dimensional array 101 as detection signals and transmits the detection signals to the main controller 109.

In step S128, the main controller 109 repeats an operation to determine whether the integrated value of the detection signals (that is, the radiation irradiation dose) has reached the threshold (target irradiation dose) based on the detection signals transmitted from the radiation imaging apparatus 100. Then, upon determining that the integrated value of the detection signals (radiation irradiation dose) has reached the threshold (target irradiation dose), the main controller 109 transmits a stop command to the exposure controller 110 in step S130. In response to this command, the exposure controller 110 controls the radiation source 112 to stop the radiation irradiation.

Next, in step S130, the main controller 109 causes the radiation imaging apparatus 100 to read each signal from the two-dimensional array 101 to obtain the signal and processes the signal in step S134.

The reading manners of signals for exposure control from the two-dimensional array 101 in the radiation imaging apparatus 100 are exemplified in FIGS. 9A to 9C. Here, for the sake of descriptive convenience, assume that the two-dimensional array 101 is formed from 7 rows. The driving signals G1 to G7 are signals supplied to the first to seventh row switches TT, that is, they are signals to select the respective first to seventh rows. "Unselected" indicates that the row has not been designated for exposure control (that is, the signals of the elements EL (detectors) of the row will not be read). "Selected" indicates that the row has been designated for exposure control (that is, the signals of the elements EL (detectors) of the row will be read). "Simultaneously Selected" indicates that the row has designated for exposure control (that is, the signals of the elements EL (detectors) of the row will be read) and that reading will be performed simultaneously. The region of interest represents a region that is to be used for exposure control out of the entire region of the two-dimensional array 101. That is, the elements EL (detectors) which belong to the region of interest and are present in each designated row can be used for exposure control.

In the reading manner shown in FIG. 9A, the elements EL (detectors) of the second, fourth, and sixth rows have been designated for exposure control. In the reading manner shown in FIG. 9B, the elements EL (detectors) of the fourth row have been designated for exposure control. In the reading manner shown in FIG. 9C, the elements EL (detectors) of the second, fourth, and sixth rows have been designated for exposure control, and the signals of these rows will be read simultaneously.

FIG. 10 schematically shows an example satisfying the condition that the minimum irradiation time Temin (=Td+Tc1+Tv+Tc2) is equal to or less than the reference irradiation time Tea in the reading manner of FIG. 9A. Note that Td is given by equation (2) as described above. TL is the time until the control signal RC changes to high level and the integrating amplifiers 131 are reset, the switches TT of the respective elements EL of the reading target row are turned on, and the signals of the elements EL are sampled and held in the corresponding sample and hold circuits 133 after the control signal SH changes to high level. In the example of FIG. 10, since Temin≤Tea, the difference between the actual radiation irradiation time Teb and the reference irradiation time Tea is small, and the accuracy of exposure control is high. Hence, the radiation dose received by the object can be suppressed to a necessary and sufficient degree. Note that the difference between the actual irradiation time Teb and the reference irradiation time Tea is the minimum irradiation time Temin at maximum. A case in which the minimum irradiation time Temin is larger than the reference irradiation time Tea represents that the difference between the actual irradiation time Teb and the reference irradiation time Tea is large (that is, the accuracy of exposure control is low) compared to a case that is otherwise.

In FIG. 11, the minimum irradiation time Temin (=Td+Tc1+Tv+Tc2) has exceeded the reference irradiation time Tea. As a result, the difference between the actual radiation irradiation time Teb and the reference irradiation time Tea is large, and the accuracy of exposure control is low. Hence, the radiation dose received by the object becomes excessive.

FIG. 12 schematically shows an example satisfying the condition that the minimum irradiation time Temin (=Td+Tc1+Tv+Tc2) is equal to or less than the reference irradiation time Tea in the reading manner of FIG. 9B. In the example of FIG. 12, since Temin≤Tea, the difference between the actual radiation irradiation time Teb and the reference irradiation time Tea is small, and the accuracy of exposure control is high. Hence, the radiation dose received by the object can be suppressed to a necessary and sufficient degree.

FIG. 13 schematically shows an example satisfying the condition that the minimum irradiation time Temin (=Td+Tc1+Tv+Tc2) is equal to or less than the reference irradiation time Tea in the reading manner of FIG. 9C. In the example of FIG. 13, since Temin≤Tea, the difference between the actual radiation irradiation time Teb and the reference irradiation time Tea is small, and the accuracy of exposure control is high. Hence, the radiation dose received by the object can be suppressed to a necessary and sufficient degree.

FIGS. 14A and 14B show two examples of a region of interest as examples of the signal reading manner for exposure control. In the reading manner shown in FIG. 14A, if Temin≤Tea is not satisfied, it is effective to change the region of interest to that of the reading manner shown in FIG. 14B. In the reading manner shown in FIG. 14B, compared to the reading manner shown in FIG. 14A, the number L of rows in which signals are read from the two-dimensional array 101 for exposure control has been decreased, and thus the minimum irradiation time Temin has been decreased.

The second embodiment of the present invention will be described below with reference to FIGS. 15 to 17. Note that matters not mentioned in the second embodiment can comply with those in the first embodiment. In the second embodiment, the arrangement of an imaging device 104 of a radiation imaging apparatus 100 is different from that of the first embodiment. FIG. 15 shows an example of the arrangement of the imaging device 104 of the radiation imaging apparatus 100 according to the second embodiment. In the second embodiment, some elements of a plurality of elements that form a two-dimensional array 101 are pixels P for capturing a radiation image, and the remaining elements of the plurality of elements are detectors S for exposure control for stopping radiation irradiation. Each of the pixels P and the detectors S can have the same arrangement as that of the element EL according to the first embodiment. The pixels P and the detectors S may have the same arrangement or have different arrangements from each other.

The imaging device 104 of the second embodiment includes a driver 211 in addition to a driver 102. The driver 102 of the second embodiment has the same arrangement as that of the driver 102 of the first embodiment. The driver 102 of the second embodiment generates, in accordance with control signals (D-CLK, DIO, XOE) supplied from the imaging controller 106, a driving signal G for controlling, for each row, the switches TT of the pixels P in the two-dimensional array 101. In addition, the driver 211 generates, in accordance with the control signals (D-CLK, DIO, XOE) supplied from the imaging controller 106, the driving signal G for controlling, for each row, the switches TT of the respective detectors S in the two-dimensional array 101. The pixels P and the detectors S can be independently selected in the second embodiment.

In the example shown in FIG. 15, the signal of each pixel P and the signal of each detector S are both read by the same signal line SL. However, an arrangement in which these signals are read by different signal lines may be employed. Also, in the example shown in FIG. 15, the detector S is provided in all of the rows formed by the pixels P. However, the detector S may be provided in only some rows out of all of the rows. Furthermore, in the example shown in FIG. 15, only one detector S is provided for each row formed by the pixels P. However, a plurality of detectors S may be provided for each row.

FIGS. 16A and 16B exemplify the reading manners of signals for exposure control from the two-dimensional array 101 of the radiation imaging apparatus 100 according to the second embodiment. Here, for the sake of descriptive convenience, assume that the two-dimensional array 101 is formed from 7 rows. Driving signals G1 to G7 are signals supplied by the driver 102 to the switches TT of the respective pixels P of the first to seventh rows, that is, they are signals to select the pixels P of the first to seventh rows. Driving signals G1' to G7' are signals supplied by the driver 211 to the switches TT of the respective detectors S of the first to seventh rows, that is they are signals to select the detectors S of the first to seventh rows.

"Unselected" indicates that the detector S of the row has not been designated for exposure control (that is, the signal of the detector of the row will not be read). "Selected" indicates that the detector S of the row has been designated for exposure control (that is, the signal of the detector S of the row will be read). The region of interest represents a region that is to be used for exposure control out of the entire region of the two-dimensional array 101. That is, the detector S which belongs to the region of interest and is present in the designated row can be used for exposure control. In the reading manner shown in FIG. 16A, the detectors S of the respective second, fourth, and sixth rows have been designated for exposure control. In the reading manner shown in FIG. 16B, the detector S of the fourth row has been designated for exposure control.

FIG. 17 schematically shows an example satisfying the condition that a minimum irradiation time Temin (=Td+Tc1+Tv+Tc2) is equal to or less than a reference irradiation time Tea in the reading manner of FIG. 16A. Note that Td is given by equation (2) as described above. TL is the time until a control signal RC changes to high level and the integrating amplifiers 131 are reset, the switches TT of respective elements EL of the reading target row are turned on, and the signals of the elements EL are sampled in the corresponding sample and hold circuits 133 after the control signal SH changes to high level. In the example of FIG. 17, since Temin≤Tea, the difference between an actual radiation irradiation time Teb and the reference irradiation time Tea is small, and the accuracy of exposure control is high. Hence, the radiation dose received by the object can be suppressed to a necessary and sufficient degree.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a national phase of PCT/JP2016/083104 filed Nov. 8, 2016, which in turn claims the benefit of Japanese Patent Application No. 2015-223337 filed Nov. 13, 2015, which are hereby incorporated by reference herein in their entirety.

The invention claimed is:

1. A radiation imaging system, comprising:
at least one radiation imaging apparatus including a two-dimensional array in which a plurality of elements that detect radiation are two-dimensionally arrayed so as to form a plurality of rows and a plurality of columns, the plurality of elements including a plurality of detectors usable for exposure control of stopping radiation irradiation in accordance with a fact that a radiation irradiation dose has reached a target irradiation dose; and
a controller, wherein
said controller is configured to determine a setting of a reading manner of reading signals from the plurality of detectors based on a radiation imaging apparatus to be used among the at least one radiation imaging apparatus, an imaging region, and object information,
the setting of the reading manner comprises designating at least two rows among the plurality of rows and, from the designated at east two rows, designating the number of rows in which simultaneous reading of signals from the detectors is to be performed, and said controller being further configured to determine, based on the setting of the reading manner, a minimum irradiation time required from the start of radiation irradiation until the stop of radiation irradiation according to signals from the two-dimensional array, the minimum irradiation time including a reading time Td required for reading the signals of the at least two rows according to Td=TL×L÷S where TL is a one-row reading time required for reading the signals of one row, L is the number of rows in which signals are read from the at least two rows and S is the number of rows in which signals are simultaneously read from the at least two rows, whereby said controller performs an error process when the minimum irradiation time exceeds a reference irradiation time, the reference irradiation time being a standard radiation irradiation time when an object having a standard physical size is to be imaged, or a time obtained by adding a positive or negative margin to the standard radiation irradiation time.

2. The system according to claim 1, wherein the error process includes a warning process of generating a warning.

3. The system according to claim 1, wherein the error process includes a process of automatically changing the reading manner so that the minimum irradiation time does not exceed the reference irradiation time.

4. The system according to claim 1, wherein the designation of the at least two rows is performed by designating a region of interest in the two-dimensional array.

5. The system according to claim 1, further comprising a radiation source configured to generate radiation, wherein
the controller performs the exposure control by controlling the radiation source.

6. The system according to claim 2, wherein the error process includes a process of changing the reading manner based on information provided by an operator.

7. A radiation imaging system comprising:
at least one radiation imaging apparatus including a two-dimensional array in which a plurality of elements which detect radiation are two-dimensionally arrayed so as to form a plurality of rows and a plurality of columns, the plurality of elements including a plurality of detectors usable for exposure control of stopping radiation irradiation in accordance with a fact that a radiation irradiation dose has reached a target irradiation dose; and a controller, wherein said controller is configured to set a default reading manner as a reading manner of reading signals from the plurality of detectors regardless of a radiation imaging apparatus to be used among the at least one radiation imaging apparatus, an imaging region, and object information, the setting of the reading manner comprises designating at least two rows among the plurality of rows and, from the designated at least two rows, designating the number of rows in which simultaneous reading of signals from the detectors is to be performed, and said controller being further configured to determine, based on the default reading manner, a minimum irradiation time required from the start of radiation irradiation until the stop of radiation irradiation according to signals from the two-dimensional array, the minimum irradiation time including a reading time Td required for reading the signals of the at least two rows according to Td=TL×L÷S where TL is a one-row reading time required for reading the signals of one row, L is the number of rows in a which signals are read from the at least two rows and S is the number of rows in which signals are simultaneously read from the at least two rows, whereby said controller performs an error process when the minimum irradiation time exceeds a reference irradiation time, the reference irradiation time being a standard radiation irradiation time when an object having a standard physical size is to be imaged, or a time obtained by adding a positive or negative margin to the standard radiation irradiation time.

8. The system according to claim 7, further comprising a radiation source configured to generate radiation, wherein
the controller performs the exposure control by controlling the radiation source.

* * * * *